United States Patent [19]
Donovan et al.

[11] Patent Number: 5,158,778
[45] Date of Patent: Oct. 27, 1992

[54] STABLE ANTIMICROBIAL DIALDEHYDE COMPOSITION AND METHODS OF USE

[75] Inventors: Daniel J. Donovan, St. Paul; David D. McSherry, Little Canada; Dale L. Fredell, Lindstrom, all of Minn.

[73] Assignee: Ecolab Inc., St. Paul, Minn.

[21] Appl. No.: 777,782

[22] Filed: Oct. 16, 1991

[51] Int. Cl.$^5$ .................. A01N 25/08; A01N 35/02
[52] U.S. Cl. .................... 424/488; 424/409; 514/705; 252/109
[58] Field of Search ............. 514/705, 947; 424/405, 424/409, 488; 428/524–526; 252/106, 109

[56] References Cited

U.S. PATENT DOCUMENTS

| | | | |
|---|---|---|---|
| 3,079,985 | 3/1963 | Boehme et al. | 514/705 |
| 3,968,250 | 7/1976 | Boucher | 424/333 |
| 4,098,859 | 7/1978 | Cummisford et al. | 264/122 |
| 4,122,192 | 10/1978 | Fellows | 424/333 |
| 4,448,977 | 5/1984 | Warner et al. | 549/201 |

FOREIGN PATENT DOCUMENTS

| | | |
|---|---|---|
| 16302/83 | 1/1984 | Australia . |
| 46375 | 2/1982 | European Pat. Off. . |
| 251743 | 1/1988 | European Pat. Off. . |
| 2605545 | 9/1976 | Fed. Rep. of Germany . |
| 3517548 | 11/1986 | Fed. Rep. of Germany . |
| 2017124 | 10/1979 | United Kingdom . |

OTHER PUBLICATIONS

Biochemists' Handbook, 1961, (pp. 30–42).
Block, "Disinfection, Sterilization, and Preservation," 1983, (p. 69).
Preservatives, Product Disclosure (Union Carbide), (p. 4).

Primary Examiner—Thurman K. Page
Assistant Examiner—Neil S. Levy
Attorney, Agent, or Firm—Merchant, Gould, Smith, Edell, Welter & Schmidt

[57] ABSTRACT

A stable, solid or semi-solid, antimicrobial composition is provided comprising a dialdehyde antimicrobial agent such as glutaraldehyde, and a carbohydrate such as a sugar or a polyol such as a sugar alcohol. The composition can be employed to preserve, sanitize, disinfect, or sterilize a contaminated surface or area. The composition can also be combined with an absorbing agent to produce a moisture absorbent antimicrobial composition which can be used to absorb and disinfect biological spills such as body fluid spills.

46 Claims, 4 Drawing Sheets

STABLE ANTIMICROBIAL DIALDEHYDE COMPOSITION AND METHODS OF USE

FIELD OF THE INVENTION

The invention relates generally to antimicrobial compositions, and more particularly to a stable antimicrobial composition comprising an adduct of a dialdehyde antimicrobial agent, and a carbohydrate or a polyol, wherein the composition regenerates the dialdehyde in active form upon the addition of an aqueous liquid.

BACKGROUND OF THE INVENTION

Antimicrobial compositions have been in use for some time and can be made of many different chemical compounds. Sodium hypochlorite is the active ingredient of many household and hospital antimicrobial products. Although disinfectants usually suffer some impairment of their activity in the presence of organic matter, the hypochlorites particularly lose much of their bactericidal potency due to the intense reactivity of both the hypochlorous acid and the hypochlorite ion with organic material generally present in the use locus. Therefore, in most instances the correct use of hypochlorite cleaning compositions requires prior removal of the organic contamination. Furthermore, chlorine containing disinfectants have an objectionable odor in use.

Saturated $C_2$ to $C_6$ dialdehydes such as glutaraldehyde are known to be particularly effective as bactericidal agents and do not have the disadvantages of other chemicals such as chlorine containing compounds. Dialdehydes and more particularly glutaraldehyde has been used for some time as a cold sterilant for sterilizing surgical instruments, catheters and for other uses in hospitals, doctors offices and dentists offices where heat sterilization is not convenient or practical, e.g., where instruments will not tolerate heat. Glutaraldehyde is most active as an antimicrobial agent above pH 7.

However, glutaraldehyde has several important shortcomings which has limited or hampered its use. Glutaraldehyde possesses a very lachrymatory vapor and an objectionable odor in an absorbed or liquid state. Glutaraldehyde in high concentrations, i.e., above about 50%, has a tendency to homopolymerize with consequent loss in microbicidal effectiveness. Moreover, the tendency to polymerize is accelerated at neutral to alkaline pHs where this compound possesses its greatest antimicrobial activity. If the pH of the aqueous glutaraldehyde is brought above pH 7 or if the water is allowed to evaporate, the glutaraldehyde will very rapidly polymerize and lose its antimicrobial activity. Therefore, glutaraldehyde must be stored at or below 50% concentration in water at a pH of less than 7 and preferably at a pH of less than 5.

Commercially available glutaraldehyde is available in 25 and 50 percent concentrations buffered on the acid side, i.e., pH 3.1-4.5 to minimize its homopolymerization during storage. Unfortunately at this pH, it possesses poor antimicrobial activity, and therefore the pH must be adjusted to 7.5-8.5 just before use. In order to overcome this problem several formulators have restored to two-part systems, the first part being a use solution, typically 2-3% glutaraldehyde buffered to pH 3.1-4.5 and, the second part consisting of an activating alkalinating agent. Since the mixed solution has a limited shelf life of several weeks, the two parts are mixed just before use. This mixing activates the glutaraldehyde by increasing its pH to the optimum level. Such two-part systems are inconvenient to use and costly to the end users in regards to shipping costs in distributing use solutions. The use of an on-site activator has been unavoidable due to the instability of aqueous glutaraldehyde at pH's above 7.

Many approaches to formulating glutaraldehyde antimicrobial compositions have been disclosed in the past. For example, U.S. Pat. No. 3,968,250 by Boucher describes the formulation of a 2% liquid glutaraldehyde composition at pH 6 to 7.4 which uses sodium citrate and an alcohol or diol to stabilize the glutaraldehyde at pH 7. Glutaraldehyde absorbed on a solid inert carrier and added to a dry alkalinating agent was disclosed in Fellows, U.S. Pat. No. 4,122,192, which demonstrated germicidal and sporicidal activity of the formulations. In another approach, Warner et al., U.S. Pat. No. 4,448,977 outlines the synthesis of a mixture of liquid acetals and acid(s) that will release glutaraldehyde after water is added to the formulation, in which the conversion to glutaraldehyde requires several hours.

European Patent Application 046 375 discloses a reduced odor glutaraldehyde formulation in which a typical formulation contained 20% of a diol and 2.5% glutaraldehyde. German Patent DE 3517548 describes a disinfectant formulation that contains 18% of an anhydrous adduct of glycerin and glutaraldehyde absorbed on a mixture of surfactant, sodium tripolyphosphate, sodium sulfate and sodium cumene sulfonate. The adduct was formed after neutralizing the glutaraldehyde to pH 6.5. Although the above patents attempt to improve the stability of glutaraldehyde in various formulations, they fail to be practical and to demonstrate long term stability of the formulations.

British Patent Application No. 2,017,124 discloses the production of resinous adducts by the reaction of difunctional aldehydes, such as glutaraldehyde, with polyols such as carbohydrate sugars or certain polyhydroxy alcohols in the presence of water. However, there is no teaching or disclosure of any antimicrobial use for these compositions.

Public health officials world-wide have a general sense of apprehension concerning spilled body fluids contaminated with the AIDS virus, hepatitis or other infectious diseases. National health authorities have consistently recommended the application of a disinfectant compound to spilled body fluids which can be contaminated such as blood, vomit, urine, or feces. Such biological spills can occur in many places including schools, hospitals, nursing homes, airplanes, restaurants, daycare centers, etc.

Moisture absorbing compositions are useful in cleaning up biological spills since they absorb liquids quickly and transform them into easily handled semi-solids. Such moisture absorbing compositions are useful in hospitals and other places where biological spills such as body fluid spills occur. Antimicrobial compositions which can be placed onto a biological spill in order to absorb and disinfect the spill area before being contacted by human hands have become increasingly important. Moisture absorbing compositions containing a chlorine source as a disinfecting agent are known. However, moisture absorbing products containing an antimicrobial dialdehyde such as glutaraldehyde are not currently available.

Therefore, there is a continuing need for a stable antimicrobial composition that can be employed in a variety of ways and provide antimicrobial action on demand.

SUMMARY OF THE INVENTION

It has now been discovered that solid dialdehyde hemiacetals with high melting points, i.e., above normal storage temperatures have excellent stability and offer formulation flexibility and possibility not heretofore possible with liquid glutaraldehyde or syrupy glutaraldehyde derivatives absorbed on solid support materials. The present invention is a stable, solid or semi-solid antimicrobial composition comprising an effective amount of an antimicrobial dialdehyde such as glutaraldehyde, and an effective stabilizing amount of a polyhydroxy compound such as a carbohydrate compound or a polyol compound, that can be used to preserve sanitize, disinfect, or sterilize a contaminated surface. The carbohydrate compound is preferably a monosaccharide compound, a disaccharide compound, an oligosaccharide compound, a polysaccharide compound, derivatives thereof, or mixtures thereof, which is employed in an amount effective to render the composition into a stable solid. The polyol compound is preferably a sugar alcohol and will render the composition into a stable semi-solid or viscous liquid. The antimicrobial composition of the invention can employ other components such as an effective amount of a buffering agent to maintain a pH range for optimum antimicrobial activity when the composition is employed in an active antimicrobial form. The antimicrobial dialdehyde is released in an active antimicrobial form when the composition of the invention is contacted with an aqueous liquid.

The composition of the invention is prepared by mixing aqueous glutaraldehyde with a polyol or carbohydrate. The water is removed under reduced pressure and/or by heating, forming adducts which are colorless, viscous liquids. Upon cooling, some of the liquids solidify to solids that can be powdered or formed into solid blocks. The prepared adducts release glutaraldehyde immediately when dissolved in water under acidic, neutral or basic conditions. The composition of the invention is formed either as an admixture of the antimicrobial dialdehyde and the carbohydrate or polyol, or is the condensation product of a reaction between a —CHO group of the dialdehyde antimicrobial agent and an —OH group of the carbohydrate or polyol.

The antimicrobial composition of the invention has excellent antimicrobial activity and does not have the associated problems which liquid glutaraldehyde has of storage instability, loss of activity, lachrymatory vapor, objectionable odor, etc. The composition is surprisingly stable in storage and surprisingly active when contacted with an aqueous liquid. The composition is particularly useful whenever an effective amount of a dialdehyde microbicide such as glutaraldehyde is needed quickly.

The solid composition of the invention can be made moisture absorbent by adding an absorbing agent for aqueous liquids such as an inorganic or organic particulate carrier material. The resulting solid, finely divided moisture-absorbent composition will effectively absorb and disinfect an aqueous liquid such as a biological spill when the composition is placed on the spill.

The antimicrobial composition can be employed in a variety of products to provide antimicrobial activity where a dialdehyde such as glutaraldehyde is preferred but its stability or liquid form in previous products have been an obstacle to its use. For example, the moisture absorbent composition of the invention can be enclosed in a packet or pouch made from a water soluble, water sensitive, or water absorbing polymeric material, to form a moisture absorbent antimicrobial article which effectively absorbs and disinfects a biological spill when the article is applied to the spill.

As used in this application, the term "antimicrobial" means having the ability to preserve, sanitize, disinfect or sterilize a contaminated surface or area through the killing of microorganisms. The terms "preserve", "sanitize", "disinfect", and "sterilize", refer to a composition's ability to increasingly kill microorganisms, from a low kill rate (preservative) up to a complete destruction of all microorganisms (sterilization).

One aspect of the invention comprises the antimicrobial composition which can be employed in various germicidal uses on contaminated surfaces. Another aspect of the invention comprises the solid, finely divided, moisture absorbent antimicrobial composition. A further aspect of the invention is an article comprising the antimicrobial composition or the moisture absorbent composition contained in a water soluble, sensitive, or absorbing polymeric material formulated into a packet or pouch. A further aspect of the invention comprises processes and methods of using the above compositions and articles in preserving, sanitizing, disinfecting, or sterilizing contaminated surfaces or areas.

DETAILED DESCRIPTION OF THE INVENTION

Figure 1:
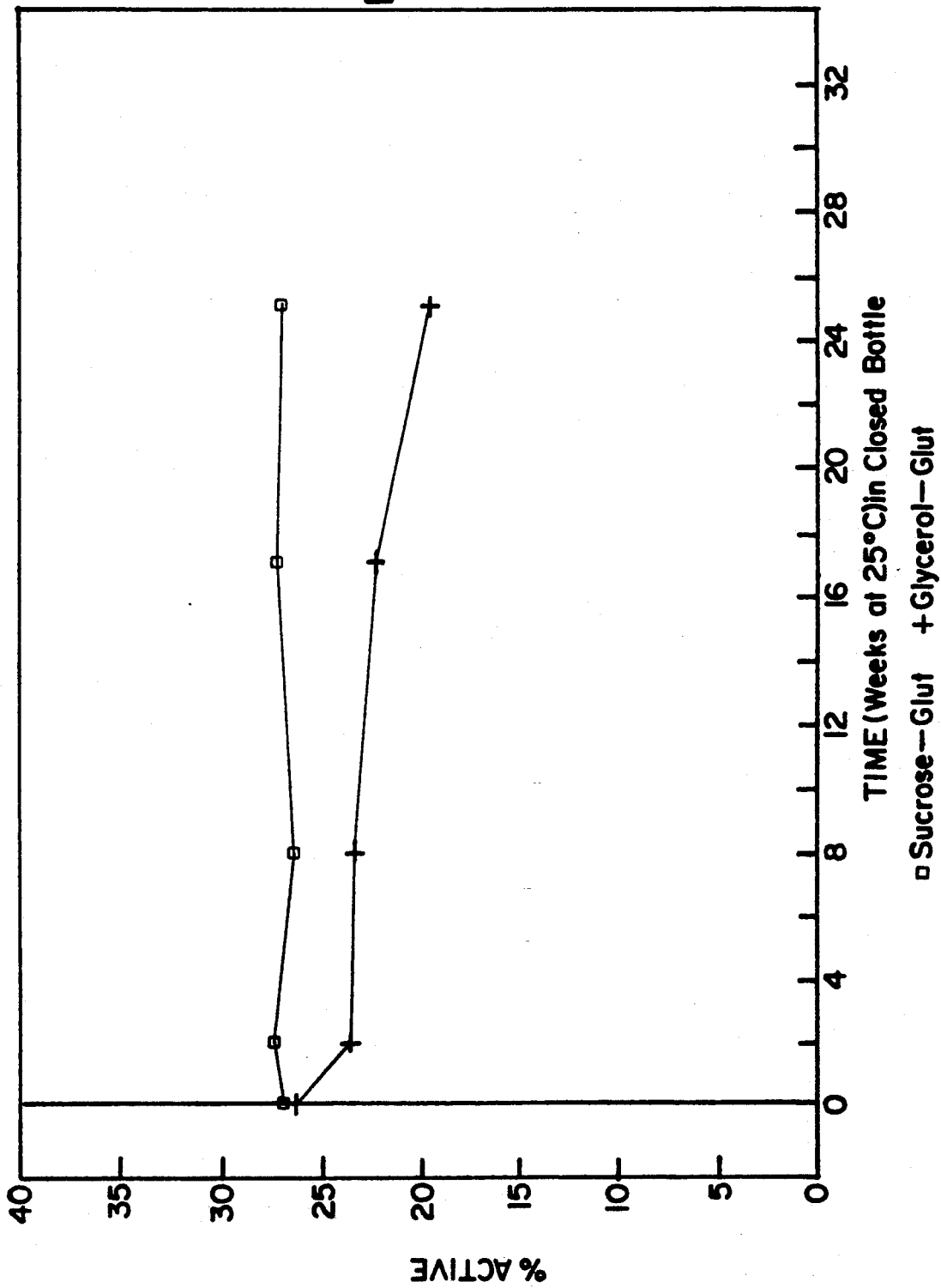
FIG. 1 is a graph demonstrating relative stabilities of a sucrose-glutaraldehyde hemiacetal of the invention compared to a prior art glycerol-glutaraldehyde hemiacetal in a closed bottle at 25° C.

The invention is a one part antimicrobial composition possessing a wide microbicidal spectrum for preserving sanitizing, disinfecting and sterilizing (e.g., having sporicidal and tuberculocidal properties) and is particularly useful as a cold sterilant in hospitals, doctors offices, dentists offices, and in veterinary practices. The composition of the invention is a stable compound comprising an antimicrobial dialdehyde and a polyhydroxy compound such as a carbohydrate compound or a polyol compound, which instantly releases the dialdehyde such as glutaraldehyde when dissolved in an aqueous media.

Antimicrobial Agent

The antimicrobial agent employed in the composition of the invention may be included in effective amounts without inducing undesirable interactions or chemical reactions between the major components of the composition of the invention. The antimicrobial agent provides the germicidal action that kills harmful microorganisms.

The antimicrobial agents employed in the composition of the invention are antimicrobial dialdehydes. Generally, these dialdehydes have the formula OHC—R—CHO, wherein R comprises a $C_1$ to $C_4$ alkylene group or a single covalent bond. In somewhat greater detail, the R group can be selected from moieties including the lower alkylenes of methylene, ethylene, propylene and butylene, or can be a single covalent bond between the two outer carbonyl groups. A preferred antimicrobial agent is a saturated $C_2$ to $C_6$ dialdehyde compound. Examples of suitable compounds include succinaldehyde, malonaldehyde, adipaldehyde, glyoxal, and glutaraldehyde.

Glutaraldehyde is particularly preferred as the antimicrobial agent and has the formula $OHC(CH_2)_3CHO$. Ucarcide 225 and 250 made by Union Carbide are available glutaraldehyde compositions that are respectively 25% and 50% active solutions. Glutaraldehyde is stable in solution at acidic pH ranges but is less active as a germicide. A typical glutaraldehyde solution is at pH 3.1 to 4.5 where it is most stable. In the alkaline pH range, glutaraldehyde solutions are more effective as germicides but are less stable, tending to polymerize.

Glutaraldehyde is one of the few microbicidal agents which possess sterilant properties, that is, an agent which is capable of destroying all forms of microbes including mycobacterium tuberculosis, viruses, spores as well as vegetative cells. Glutaraldehyde is in demand particularly for sterilizing surgical instruments and supplies and more, especially in situations where heat sterilization is not practical or where heat may damage the article being sterilized.

As previously indicated, glutaraldehyde has a great tendency to homopolymerize at pH ranges in which it is most active. Thus, glutaraldehyde for microbicidal uses has heretofore always been sold as an aqueous solution, generally at 25 to 50 percent active strength for commercial use, or at a use concentration usually at 2–3 percent active strength, at a pH in the range of 3.1–4.5 for end uses in order to avoid homopolymerization during the time it is manufactured to the time it is used. This has meant that an alkalinating agent must be added just prior to use to adjust the pH of the use solution to the range of about pH 8 to 9. This has required a two-part system in prior products making them inconvenient to use, requiring premeasured amounts of each part to insure that the pH is in the correct range.

The importance of the pH adjustment of the glutaraldehyde cannot be overemphasized. For example, the rate of kill at pH 8.5 is approximately twenty times faster than at pH 5.0. The difference is presumably caused by the slower reaction rate of this biocide when surface amine groups of the cell wall at the acidic pH are protonated or form amine salts. In this state, it is believed that glutaraldehyde derives its activity by penetrating the cell wall where the internal pH is more neutral and reacts with internal free amine moieties. The lower the pH, the more surface amines that will be protonated and greater the biocidal lag.

Different mechanisms for the inactivation of bacteria by antimicrobial agents such as glutaraldehyde have been considered in order to explain the mode of antimicrobial action. One notion is that the ultimate bactericidal effect appears to be due to the ability of these agents to cause a release of the bacterial cell content into the surrounding medium. It is also thought that the interaction of the antimicrobial agent with the cell wall interferes with the metabolic processes of the organism, causing the killing action.

The antimicrobially effective composition of the invention can comprise about 1 to 90 wt-% of the antimicrobial dialdehyde such as glutaraldehyde, preferably about 20 to 70 wt-%, and most preferably about 50 to 60 wt-% based on the antimicrobial composition.

Carbohydrates and Polyols

The antimicrobial composition of the invention additionally employs an effective stabilizing amount of a polyhydroxy compound comprising a carbohydrate compound such as a sugar, or a polyol compound such as a sugar alcohol.

Sugars are a group of organic compounds related by molecular structure that comprise simpler members of the general class of carbohydrates. Each sugar consists of a chain of 2 to 7 carbon atoms (usually 5 or 6). One of the carbons carries aldehydic or ketonic oxygen which may be combined in acetal or ketal forms and the remaining carbon atoms usually bear hydrogen atoms and hydroxyl groups. In general, sugars are more or less sweet, water soluble, colorless, odorless, optically active substances which lose water, caramelize and char when heated.

Some sugars exist as discrete single units called monoses or monosaccharides. Others are coupled into di, tri, and higher saccharides. Carbohydrates that break up on hydrolysis to produce two monosaccharides are called disaccharides. Disaccharides are formed by condensation of two monosaccharides through one or both of the carbonyl groups. The new linkage is labile to acid and often to alkali. Acids will hydrolyze a disaccharide to its constituent monosaccharides, and disaccharides which have a free carbonyl group show reducing properties. As used in the present specification, the term "oligosaccharide" denotes a sugar polymer of from 3 to 15 units, and a higher sugar polymer having more than 10 units is designated as a "polysaccharide".

The carbohydrate component of the composition of the invention preferably comprises one or more monosaccharides, disaccharides, oligosaccharides, polysaccharides, derivatives thereof, or mixtures thereof. The monosaccharide employed preferably comprises fructose, glucose, or mixtures thereof. The disaccharide preferably comprises sucrose, lactose, maltose or mixtures thereof. The carbohydrate component of the composition of the invention can also comprise a disaccharide, an oligosaccharide, a polysaccharide, or mixtures thereof that comprise repeating units of glucose. When a carbohydrate is employed it renders the compositions of the invention into a stable solid.

Glucose (dextrose) is known commercially as corn sugar and occurs in the free state in fruit juices and together with fructose in honey. Commercial sources of glucose include acid or enzyme hydrolyzed corn starch. The most common form of glucose is the monohydrate of the alpha form called dextrose hydrate (melting point 80°–85° C). Fructose (levulose) occurs with glucose in honey, but more commonly they are combined in sucrose. As a fructose polymer, it is a storage carbohydrate in the tubers of the dahlia and the Jerusalem artichoke, as well as the Hawaiian ti plant. D-fructose is the most soluble of the common sugars and crystallizes in an anhydrous beta form (melting point 102°–104° C.) which is hygroscopic.

Sucrose is a disaccharide made up of the monosaccharides of glucose and fructose in which an α-D- glucosyl residue in a six membered ring form is combined with a β-D-fructoside residue in the five membered ring form. Sucrose has been found in the juice of every land plant examined for it and is mainly produced from sugar cane and beets. Sucrose crystallizes from water in a characteristic monoclinic form (melting point 184° C.). Lactose, or milk sugar, is a disaccharide which has been found to comprise about 2 to 6% of the milks of all mammals studied. The commercial product is the monohydrate of the alpha form (melting point 201.6° C.). If crystallized at temperatures above 93.3° C. the anhydrous beta form is produced (melting point 252.2° C.). In lactose, a beta-galactosyl residue is combined to the hydroxyl oxygen on the fourth carbon of a glucose unit, and both moieties are in six membered ring form, making lactose a reducing sugar. Maltose, or malt sugar, is a disaccharide which occurs in sprouted grain, and in the malting stage of the brewing process. Maltose is produced commercially by degrading starch with a beta-amylase. Maltose is a reducing disaccharide in which an alpha glucosyl residue is attached to the hydroxyl oxygen on the fourth carbon of another glucose unit, with both glucoses in their six membered ring forms. Maltose crystallizes from water as the monohydrate of the beta form (melting point 102°-103° C.).

Various oligosaccharides and polysaccharides can also be employed in the composition of the invention. Preferred oligosaccharides are derivatives of sucrose. Polysaccharides are widely distributed in the plant and animal worlds and serve as a food reserve substance and structural material. Suitable polysaccharides include starch and cellulose, which consist of D-glucopyranosyl units linked by α- and β-1,4 bonds, respectively. Cornstarch is a preferred polysaccharide for use in the composition of the invention.

The carbohydrate compound employed in the composition of the invention may also comprise various derivatives of the above sugars, preferably ester or ether derivatives of the sugars. Esters of carbohydrates are normally produced by treating the carbohydrate with an acid chloride or an acid anhydride in the presence of a base. All of the hydroxyl groups of the carbohydrate react, including the anomeric one. Carbohydrates can be converted into ethers by treatment with an alkyl halide in the presence of a base. Complete etherification is achieved only after repeated treatment. Ester and ether derivatives of carbohydrates can be used since they are easier to work with than some free sugars. Because of their many hydroxyl groups, the monosaccharides are usually quite soluble in water, but they are insoluble in organic solvents. They are also difficult to purify and have a tendency to form syrups rather than crystals when water is removed. Ester and ether derivatives, however, behave like most other organic compounds in that they tend to be soluble in organic solvents and to be readily purified and crystallized.

The polyols that can be employed in the composition of the invention are polyhydroxyl alcohols having 3 or more hydroxyl groups per molecule. Polyols with greater than three hydroxyl groups are generally known as sugar alcohols and have the formula $CH_2OH(CHOH)_nCH_2OH$, wherein n may be from 2 to 5. Examples of suitable polyols include xylitol, maltitol, pentaerythritol, mannitol, sorbitol, inositol, glycerol, ethylene glycol, 1,4-cyclohexane diol, etc. When the polyols are employed in the composition of the invention, they render the antimicrobial agent into a semisolid or viscous liquid.

The antimicrobial composition comprises about 10 to 99 wt-% of the carbohydrate or polyol compound, preferably about 30 to 80 wt-%, and most preferably about 40 to 50 wt-% based on the antimicrobial composition. The solid form of the antimicrobial composition of the invention can be formed into a particulate having any desired particle size. The composition of the invention may also be formed into a solid block.

Buffering Agent

The antimicrobial composition of the invention can employ buffering agents so that the composition is maintained in an alkaline pH range when employed in an active antimicrobial form. Buffering agents are preferably employed that will maintain the pH at an optimum alkaline level for antimicrobial activity of the dialdehyde, such as glutaraldehyde, when the composition is contacted with an aqueous liquid. A useful pH range for antimicrobial activity of the composition of the invention is about 3 to 11, preferably about 7 to 9.

Typical buffering agents which may be employed include sodium bicarbonate/sodium carbonate, acetic acid/sodium acetate, potassium dihydrogen phosphate/disodium hydrogen phosphate, cacodylic acid/sodium cacodylate, tris(hydroxymethyl) aminomethane hydrochloride/ tris(hydroxymethyl) aminomethane, barbitone/barbitone sodium, potassium p-phenolsulphonate/potassium sodium p-phenolsulphonate, 2-amino-2-methylpropane-1,3-diol hydrochloride/2-amino-2-methylpropane-1,3-diol, ammonia/ammonium chloride, glycine/sodium glycinate, tris acid maleate/sodium hydroxide, potassium dihydrogen phosphate/sodium hydroxide, hydrochloric acid/collidine, hydrochloric acid/tris(hydroxymethyl) aminomethane, hydrochloric acid/2-amino-2-methylpropane-1,3-diol, boric acid/potassium chloride/sodium hydroxide, and disodium hydrogen phosphate/sodium hydroxide. Other suitable inorganic buffers include borax (sodium borate), calcium carbonate, ferrous hydroxide, lime (calcium carbonate), sodium hydrogen carbonate, sodium hydrogen phosphate, sodium hydroxide, sodium dihydrogen phosphate, sodium metasilicate, sodium sesquicarbonate, sodium oxide, and trisodium phosphate. Suitable organic buffers include sodium benzoate, sodium citrate, sodium fumarate, sodium glutarate, sodium lactate, sodium laurate, sodium oleate, sodium oxalate, sodium salicylate, sodium stearate, sodium succinate, sodium tartrate, monoethanolamine, diethanolamine, and triethanolamine.

The antimicrobial composition can comprise about 0 to 30 wt-% of the buffering agent, preferably about 1 to 20 wt-%, and most preferably about 1 to 5 wt-% based on the antimicrobial composition.

Absorbing Agent

The solid form of the antimicrobial composition of the invention can be combined with an absorbing agent for aqueous liquids comprising a dry inorganic or organic particulate carrier material to produce a moisture absorbent composition. The antimicrobial composition is preferably finely divided and blended with a dry powdered carrier material to produce a flowable disinfectant powder mixture. The absorbing agent effectively aids the antimicrobial composition in absorbing an aqueous liquid such as a biological spill when the composition is applied to the spill. Carrier material absorbing agents which can be used in the present invention include silica, an alkali metal silicate, polyacrylate, diatomaceous earth, ground corn cobs or mixtures thereof.

The silica or silicon dioxide ($SiO_2$) which can be employed as the absorbing agent is preferably amorphous. Amorphous silicas are substantially dehydrated, polymerized silicas which may be considered as condensation polymers of silicic acid. The preferred amorphous silica for use in the composition of the invention is precipitated silica. Precipitated silica is a very fine divided silica in which the degree of polymerization is limited by the preparation technique. Precipitated silicas are formed by the destabilization of soluble silicates, usually accomplished by acid neutralization. The destabilization is carried out in a solution which also contains polymerization inhibitors, such as inorganic salts, which cause an extremely fine precipitate of hydrated silica to be formed. This precipitate is then filtered, washed essentially free of occluded salts, and dried to the desired degree. The ultimate silica particle has a size of about 20-50 m$\mu$ (millimicrons) and forms an agglomerated particle of 1-5$\mu$ (microns). Precipitated silicas have a surface area of about 100-200 $m^2$ per gram and are often contaminated with calcium or other cations from the precipitating salt. The percent of silicon dioxide ($SiO_2$) in precipitated silica is from 85 to 90% and the pH can range from about 4 to 8.5.

Another absorbing agent which can be blended with the antimicrobial composition of the invention is an alkali metal silicate. Alkali metal silicates are synthetic inorganic silicates formed with an alkali metal base. A preferred alkali metal silicate for use in the composition of the invention is sodium silicate in anhydrous powdered or crystalline hydrated form. Other silicates which can be employed include potassium or lithium silicates. Sodium silicate has a moderately basic pH and can vary from about 0.5 $SiO_2/Na_2O$ to 4 $SiO_2/Na_2O$. Crystalline products which are commercially available are the anhydrous sodium metasilicate and the hydrated metasilicates. Typically, sodium and potassium silicates are manufactured in ordinary glass furnaces by melting sand with soda ash at about 1450° C. The ratio of the components is determined by the proportion of sand and alkali added to the furnace. Commercial soda ash is quite pure and makes little contribution to the impurities in the final product. The anhydrous crystalline products may be made by melting sodium carbonate and sand at the intended ratio. Such glasses crystallize very rapidly, but the higher the proportion of sodium carbonate the greater the proportion of carbon dioxide retained in the melting crystals. Therefore, the anhydrous solids which are more alkaline than the hydrated metasilicates are often mechanical or integral mixtures of sodium metasilicate and caustic soda. The hydrated crystalline products are usually formed by preparing a solution of the hydrate composition at a temperature above the melting point and cooling and crystallizing the mass.

Another absorbing agent which can be combined with the antimicrobial composition of the invention to produce a moisture absorbent antimicrobial composition is a porous polymeric moisture absorbing composition such as polyacrylate. Sanwet ® available from Hoechst Celanese is a preferred polyacrylate polymer composition. Another preferred moisture absorbing composition is diatomaceous earth which is a soft and bulky solid material (about 88% silica) composed of skeletons of small prehistoric aquatic plants related to algae (diatoms). Celatom FW-80 from Eagle-Picher is a preferred diatomaceous earth. Ground corn cobs may also be employed as an absorbing agent.

The above absorbing agents can be employed singly or in various mixtures in formulating the moisture absorbent composition of the invention. The moisture absorbent antimicrobial composition comprises about 0 to 99 wt-% of the absorbing agent, preferably about 50 to 99 wt-%, and most preferably about 70 to 99 wt-% based on the antimicrobial composition.

Other Components

In addition to the above mentioned components, the composition of the invention may also contain conventional additives such as pigments, fragrances, anticorrosion agents, stabilizers such as triethylene glycol, and surfactants. Surfactants which can be employed in the composition of the invention include quaternary ammonium compounds, nonionic and anionic surfactants. Quaternary ammonium compounds not only function as surfactants but aid in antimicrobial activity. Nonionic surfactants can provide increased stability to the antimicrobial composition. Preferred nonionic surfactants are water insoluble alcohols such as octanol, decanol, dodecanol, etc.; phenols such as octyl phenol, nonyl phenol, etc.; and ethoxylates of the above-mentioned alcohols and phenols, with from 1 to 10 moles of ethylene oxide per mole of alcohol or phenol preferred. Other nonionic surfactants which can be used include ethylene oxide/propylene oxide block copolymers. When surfactants are employed they can comprise about 0 to 89 wt-%, preferably about 1 to 50 wt-% of the composition of the invention.

A preferred solid, antimicrobial composition comprises about 1 to 90 wt-% of an antimicrobial agent having the following formula: OHC—R—CHO, wherein R comprises a $C_1$ to $C_4$ alkylene group or a single covalent bond; about 10 to 99 wt-% of a polyhydroxy compound comprising a carbohydrate compound, a polyol compound comprising a sugar alcohol, or mixtures thereof, with the carbohydrate selected from the group of monosaccharide compounds, disaccharide compounds, oligosaccharide compounds, polysaccharide compounds, derivatives thereof, or mixtures thereof and about 0 to 30 wt-% of a buffering agent that can maintain a pH of about 3 to 11 for optimum antimicrobial activity of the composition when it is in activated form.

A particularly preferred solid, stable antimicrobial hemiacetal composition comprises about 1 to 90 wt-% of glutaraldehyde, and about 10 to 99 wt-% of sucrose.

A preferred solid, finely divided, moisture absorbent antimicrobial composition comprises about 2 to 50 wt-% of an antimicrobial dialdehyde compound; about 1 to 50 wt-% of a polyhydroxy component comprising a carbohydrate compound, a polyol compound comprising a sugar alcohol, or mixtures thereof, with the carbohydrate selected from the group of a monosaccharide compound, a disaccharide compound, an oligosaccharide compound, a polysaccharide compound, derivatives thereof, and mixtures thereof; and about 10 to 97 wt-% of an absorbing agent for aqueous liquids selected from the group consisting of precipitated silica, a silicate, polyacrylate, diatomaceous earth, ground corn cobs, or mixtures thereof. The moisture absorbent composition effectively absorbs an aqueous liquid such as an aqueous spill site.

The present invention provides a stable, solid dialdehyde donor which instantly releases the dialdehyde upon dissolving in an aqueous medium. It is believed that the composition of the invention is formed either as an admixture of the antimicrobial agent and the carbohydrate or polyol acting as a carrier, or is formed as a condensation product. It is likely that a —CHO group of the dialdehyde antimicrobial agent such as glutaraldehyde reacts with an —OH group of the carbohydrate or polyol to bond the agent to the carbohydrate or polyol in a condensation reaction, forming the composition of the invention. Glutaraldehyde can form hydrates, hemiacetals or acetals in an aqueous sucrose solution. Since water is removed to form the present composition, it would seem likely that hemiacetals are being formed between glutaraldehyde and the sugar. Due to the multiple hydroxyl groups of a sugar such as sucrose and the dialdehyde groups of glutaraldehyde, it is possible to form both intra- and intermolecular hemiacetals. The former could form molecules and the latter could form polymers. It is probable that a mixture of structures are found in the present composition.

We have discovered that the hemiacetals of the invention are very stable and certain solid forms of hemiacetal are among the most stable. A particularly preferred hemiacetal is a solid glutaraldehyde-sucrose hemiacetal. We have also discovered that these hemiacetals readily form free glutaraldehyde upon dissolving in an aqueous system and are as active as free glutaraldehyde on a ppm by ppm comparison with glutaraldehyde.

The solid glutaraldehyde hemiacetals of the invention are particularly desirable and advantageous in that they may be formulated with other solid alkalinating or buffer agents, solid surfactants and other solid components without interaction with these additives, thus providing a one-part system, i.e., a measured portion is dissolved in a given volume of water to obtain a fully active use solution. Further advantages over prior disclosed products are that inert, undesirable support materials are not needed, and a concentrated product may be formulated; in short, the present invention has economic advantages in that fillers (support materials) are not required and there would thus be savings in shipping and storage costs. These stable systems thus fulfill an unmet need not disclosed by the prior art. The composition of the invention has excellent antimicrobial activity and does not have the associated problems which liquid glutaraldehyde has of storage instability, loss of activity, lachrymatory vapor, objectionable odor, etc.

The present invention also has toxicity levels which are safer than prior glutaraldehyde preparations. The LD (lethal dose) is the same in either case for oral ingestion, however, the skin toxicity is reduced in the present composition provided in solid form since the solids are not absorbed through the skin. For example in rats, aqueous glutaraldehyde has an $LD_{50}$ of 2.38 ml/kg when taken orally and an $LD_{50}$ of 2.56 ml/kg through the skin. The lethal dose is much higher when the present composition in solid form is contacted with the skin, thus providing a safer product for handling.

Methods of Making

The antimicrobial composition of the invention can be a solid source of an antimicrobial dialdehyde such as glutaraldehyde. A hard, clear, crystalline solid can be produced by hot (e.g., 80° C.) dehydration of an aqueous glutaraldehyde-sugar solution. The antimicrobial composition can be made odorless by baking, is stable in warm air and has a melting point of 60°–80° C.

In a typical synthesis, water is removed without any problems under reduced pressure with a water aspirator and with temperatures in the range of 50° to 100° C. In the preparation of a glutaraldehyde-sucrose adduct composition, the mixture becomes extremely viscous and water removal stops using the above conditions. Two processes were discovered to manufacture the glutaraldehyde-sucrose composition and circumvent the above barrier. The high viscosity was found to be localized in the center of the resin flask, which was related to temperature gradients in the resin flask. The viscosity can be kept homogeneous by using a higher reduced pressure or a viscosity reducer (e.g., glycerin) which results in a more uniform temperature throughout the resin flask.

The processes which can be used in preparing stable compositions of the invention high in activity are pH and temperature sensitive. If the composition is prepared at pH's above 6, the measured glutaraldehyde activity is low. The compositions with the best activity are prepared with 25% and 50% commercial glutaraldehyde, whose pH is 3.1 to 4.5.

After preparation, the compositions of the invention possess a high glutaraldehyde activity and the ability to release glutaraldehyde instantaneously in water. However, the ability of the compositions to release glutaraldehyde decreases with time. Each composition has a different stability and is dependent upon the processing conditions. The glutaraldehyde-sucrose composition shows a surprisingly superior long term ability to release a constant amount of glutaraldehyde.

Antimicrobial studies with the composition of the invention (dissolved in water) indicate it behaves exactly like liquid glutaraldehyde. The composition of the invention is completely soluble in water and evidence from NMR (Nuclear Magnetic Resonance) studies indicate that only the sugar and glutaraldehyde are found in an aqueous solution. This would indicate that the solid composition readily releases glutaraldehyde in water.

The composition of the invention can be provided in various solid forms. These include powders, pastilles (hardened droplets), granulate, and solid blocks of varying sizes. The solid form of the invention is higher than 50% active and can be up to as high as 80% active. The moisture absorbent antimicrobial composition can be made by blending the absorbing agent with the preformed antimicrobial dialdehyde composition which has been finely divided into a solid particulate form.

Unlike liquid glutaraldehyde, the composition of the invention is surprisingly very stable alone or in formulated products, and is antimicrobially effective in the presence of a dry base. The composition thus is able to mimic glutaraldehyde where glutaraldehyde would be preferred, but its stability or liquid state is an obstacle. For example, the solid antimicrobial composition can be employed in various products where an antimicrobial agent is useful such as in lubricants, as well as in urinal and toilet rim blocks. The dialdehyde-sugar composition can be formulated with dry bases and/or with absorbents without loss of antimicrobial activity. The dialdehyde-sugar composition can also be molded into blocks. The blocks themselves have utility as sanitizers and disinfectants. The blocks or powders can be formulated with dry bases and when dissolved in an aqueous liquid can be used as cold sterilizing agents for medical equipment.

The antimicrobial composition combined with the absorbing agent to produce the moisture absorbent antimicrobial composition can be employed in containers such as water soluble, water sensitive or water absorbing polymeric materials formulated into packets or pouches, to provide an absorbent disinfectant article. The absorbent article can be used to clean up biological spills such as contaminated body spills that are found in hospitals and other areas.

A preferred moisture absorbent antimicrobial article comprises a solid, finely divided, moisture absorbent antimicrobial composition of about 2 to 50 wt-% of an antimicrobial saturated $C_2$ to $C_6$ dialdehyde compound; about 10 to 97 wt-% of an absorbing agent for aqueous liquids; and about 1 to 50 wt-% of a carbohydrate compound comprising a disaccharide compound, an oligosaccharide compound, a polysaccharide compound, or mixtures thereof. The article also comprises a water soluble, water sensitive, or water absorbing polymeric material formed into a packet or pouch which contains the moisture absorbent antimicrobial composition. The article can effectively absorb and disinfect a spill site of an aqueous liquid when the article is applied to the spill. The preferred components of the moisture absorbent composition are the same as that described previously. The preferred polymeric material used in the article and formed into a packet or pouch is made of a polyvinyl alcohol polymer.

Methods of Use

A method of preserving, sanitizing, disinfecting or sterilizing a contaminated surface or area using a stable antimicrobial composition comprising an effective amount of an antimicrobial dialdehyde compound, and an effective amount of a polyhydroxy component comprising a carbohydrate compound, a polyol compound, or mixtures thereof, comprises the steps of contacting the composition in activated form with the contaminated surface or area for a period of time effective to preserve, sanitize, disinfect or sterilize the surface or area.

The moisture absorbent composition and the article containing the moisture absorbent composition are particularly useful in cleaning up and disinfecting aqueous biological spill areas produced by body fluid spills. Such spills can comprise aqueous biohazards or aqueous biocontaminants. The moisture absorbent composition and article of the invention provide for safe, easy disposal of biological spills that can be hazardous. The composition and article provide a safe means for cleanup of biological spills since the composition is sprinkled or the article is placed onto the spill before human contact, absorbing and disinfecting the spill before it is picked up and disposed of.

A process for cleaning and disinfecting a biological spill using the solid, moisture absorbent antimicrobial composition described above comprises the steps of contacting the antimicrobial composition with the biological spill for a period of time effective to absorb and disinfect the biological spill. A process for cleaning and disinfecting a biological spill using a moisture absorbent antimicrobial article comprising a solid moisture absorbent antimicrobial composition as described above and a water soluble, water sensitive, or water absorbing polymeric material formulated into a packet or pouch which contains the moisture absorbent antimicrobial composition, comprises the steps of contacting the antimicrobial article with the biological spill for a period of time effective to absorb and disinfect the biological spill.

Antimicrobial solutions can also be prepared by using the composition of the invention comprising the dialdehyde antimicrobial agent such as glutaraldehyde, and the carbohydrate or polyol compounds. The composition is mixed with an aqueous liquid to form a preserving, sanitizing, disinfecting, or sterilizing solution which can be then be contacted with contaminated objects and articles. Examples of such objects and articles include contaminated medical instruments and tools, as well as contaminated clothing or other fabrics.

A moisture sensitive antimicrobial article which can be used to prepare a preserving, sanitizing, disinfecting, or sterilizing solution comprises about 1 to 90 wt-% of an antimicrobial saturated $C_2$ to $C_6$ dialdehyde, and about 10 to 99 wt-% of a polyhydroxy component comprising a carbohydrate compound or a polyol compound. The antimicrobial composition is contained in a water soluble, water sensitive, or water absorbing polymeric material formed into a packet or pouch. The article can be added to an aqueous liquid to form an aqueous preserving, sanitizing, disinfecting, or sterilizing solution. The polymeric material employed is preferably a polyvinyl alcohol polymer.

A method of preserving, sanitizing, disinfecting, or sterilizing contaminated objects or articles comprises the steps of adding the above antimicrobial article to an effective dissolving amount of an aqueous liquid, thereby forming an aqueous antimicrobial solution. The contaminated objects or articles are then contacted with the antimicrobial solution for a period of time effective to preserve, sanitize, disinfect, or sterilize the objects or articles.

The following Examples are illustrative of the invention and contain a best mode.

EXAMPLE 1

The antimicrobial composition of Example 1 was made by the following procedure. Into a round bottom flask, 34 grams of deionized water was added to 30 grams of 50% aqueous glutaraldehyde, followed by the addition of 34.23 grams of sucrose. The solution was heated on a steam bath until all the sucrose dissolved, forming a clear homogenous solution. The reaction solution was stripped of its volatiles on a rotary evaporator at 80° C. The resulting product was a hard, clear, crushable foam comprising glutaraldehyde and sucrose.

The antimicrobial activity of Example 1 was then tested as well as its glutaraldehyde releasing properties by comparison with Ucarcide 250 (50% aqueous glutaraldehyde). Several experiments were performed to test the antimicrobial activity of Example 1. The first experiment involved dissolving the solid composition of Example 1 in neutral, unbuffered water to produce a theoretical 1250 ppm concentration of glutaraldehyde. The active solutions were inoculated with the respective organisms of S. aureus and E. coli and population reductions were measured versus time (see Table I). A second experiment was performed in exactly the same manner as the first except that the pH of the active solution was buffered to pH 8 (see Table II). The data from Table I and Table II demonstrate that the composition of Example 1 had the same antimicrobial activity as aqueous glutaraldehyde and that Example 1 released 100% of its glutaraldehyde.

TABLE I

Antimicrobial Testing of Example 1

| Sample | Exposure Time (Minutes) | Log Reductions S. aureus | Log Reductions E. coli |
|---|---|---|---|
| Example 1 | 0.5 | 2.24 | 0.30 |
| (Glutaraldehyde | 1.0 | 3.43 | 0.59 |
| /Sucrose)[1] | 2.0 | >5.00 | 0.85 |
|  | 5.0 | >5.00 | 2.03 |
| Ucarcide 250[2] | 0.5 | 2.64 | 0.34 |
|  | 1.0 | 4.00 | 0.47 |
|  | 2.0 | >5.00 | 0.85 |
|  | 5.0 | >5.00 | 1.74 |

[1] At theoretical 1250 ppm glutaraldehyde
[2] 50% aqueous glutaraldehyde at 1250 ppm use concentration

TABLE II

Antimicrobial Testing of Example 1 at pH 8

| Sample | Exposure Time (Minutes) | Log Reductions S. aureus | Log Reductions E. coli |
|---|---|---|---|
| Example 1 | 0.5 | >5.00 | 3.51 |
| (Glutaraldehyde/ | 1.0 | >5.00 | 3.81 |
| Sucrose)[1] | 2.0 | >5.00 | >5.00 |
|  | 5.0 | >5.00 | >5.00 |
| Ucarcide 250[2] | 0.5 | >5.00 | 3.92 |
|  | 1.0 | >5.00 | >5.00 |
|  | 2.0 | >5.00 | >5.00 |
|  | 5.0 | >5.00 | >5.00 |

[1] At theoretical 1250 ppm glutaraldehyde.
[2] 50% aqueous glutaraldehyde at 1250 ppm use concentration.

Test concentrations were used at a theoretical 1250 ppm glutaraldehyde. This assumes that Ucarcide 250 contains 50% active glutaraldehyde and Example 1 contains 30.5% available glutaraldehyde. The actual values were obtained from the titration assay (see Table III).

The "hot air" stability and glutaraldehyde releasing properties of Example 1 were tested by open exposure in an oven followed by titration (See Table III).

TABLE III

Assay of Example 1 for Glutaraldehyde Content

| Exposure time (at 50° C.) | Percent Glutaraldehyde |
|---|---|
| 0 hours (freshly prepared) | 26.0%* |
| 15 hours | 23.7% |
| 336 hours (two weeks) | 23.0% |

*Theoretically, Example 1 should contain 30.5% active glutaraldehyde.

As indicated in Table III, Example 1 retained most of its glutaraldehyde after a two week exposure at 50° C.

Additional samples of Example 1 were prepared having differing levels of glutaraldehyde. The stability of these sucrose-glutaraldehyde addition products were tested and the results are summarized in Table IV below.

TABLE IV

| Sample | Theor. Activity | Initial Corrected Activity | Activity After 6 Wks/40° C. | [1]Δ/Theor. | [2]Δ/Init. |
|---|---|---|---|---|---|
| 1 | 2.00% | 1.73% | 1.57% | 0.43 | 0.16 |
| 2 | 10% | 8.65% | 8.07% | 1.93 | 0.58 |
| 3 | 30% | 25.9% | 24.3% | 5.7 | 1.60 |
| 4 | 50% | 43.1% | 42.2% | 7.8 | 0.90 |
| 5 | 60% | 50.9% | 51.2% | 8.8 | 0.30 |
| 6 | 70% | 59.4% | 57.9% | 12.1 | 1.50 |
| 7 | 80% | 66.5% | 65.9% | 14.1 | 0.60 |
| 8 | 90% | 66.2% | 74.4% | 15.6 | 8.2 |

[1] Δ/Theor.: The change from final to theoretical in (absolute) activity (process related).
[2] Δ/Initial: The change from final to initial in (absolute) activity.

As Table IV indicates, samples 5 to 8 actually gained in activity after 6 weeks, while the other samples had minimal losses in activity over the same time period.

EXAMPLES 2-10

The following Examples were prepared by a similar procedure as discussed above for Example 1. Examples 2-10 were addition products of glutaraldehyde and various polyhydroxy compounds of carbohydrates and polyols. The various polyhydroxy components and characteristics of these compositions are listed in Table V below.

TABLE V

| Examples (Polyhydroxy) | Moles of Hydroxy/Glutar. | Melting Point of Examples | Melting Point of Polyhydroxy | Theoretical Activity | Initial Corrected Activity |
|---|---|---|---|---|---|
| Ex. 2 (Sucrose) | 2.00/3.00 | 60–80° C. | 185–87° C. | 30.5% | 26.4 |
| Ex. 3 (Lactose) | 1.00/1.00 | 55–70° C. | 253–55° C. | 22.0% | 18.7 |
| Ex. 4 (Fructose) | 1.00/1.00 | >RT[1] | 100° C. | 36% | 29.2 |
| Ex. 5 (Glucose) | 2.00/1.00 | >RT | 153–56° C. | 22% | 18.4 |
| Ex. 6 (Pentaerythritol) | 1.00/2.00 | 49–60° C. | 255–59° C. | 59.5% | 51.8 |
| Ex. 7 (Mannitol) | 1.00/1.00 | >RT | 167–70° C. | 36% | 28.5 |
| Ex. 8 (Sorbitol) | 1.00/1.00 | 80° C. | 98–100° C. | 36% | 27.7 |
| Ex. 9 (Sucrose[2] Ester) | 1.00/1.00 | >RT | — | 16% | 3.64 |
| Ex. 10 (Inositol) | 1.00/1.00 | >RT | — | 36% | 22.6 |

[1] RT = Room Temperature
[2] Lauric ester of sucrose. L1695 (Ryoto Sugar Esters, Inc.)

The antimicrobial activity of Examples 2, 3 and 6 was tested along with a stock sample of Ucarcide 250 for their antimicrobial activity. The Examples were tested at a buffered pH 8 by a similar procedure as described in Example 1. The results of the study are listed in Table VI below. The data from Table VI indicates that the compositions of Examples 2, 3, and 6 have the same antimicrobial activity as aqueous glutaraldehyde.

TABLE VI

Antimicrobial Testing

| Sample | pH | Exposure Time (Minutes) | Log Reduction S. aureus | Log Reduction E. coli |
|---|---|---|---|---|
| Ex. 2 | 8 | 0.5 | >5.0 | 2.62 |
| (Glutaraldehyde/ |  | 1.0 | >5.0 | 3.81 |
| Sucrose) |  | 2.0 | >5.0 | >5.0 |
|  |  | 5.0 | >5.0 | >5.0 |
| Ex. 3 | 8 | 0.5 | >5.0 | 4.28 |
| (Glutaraldehyde/ |  | 1.0 | >5.0 | >5.0 |
| Lactose) |  | 2.0 | >5.0 | >5.0 |
|  |  | 5.0 | >5.0 | >5.0 |
| Ex. 6 |  | 8 | 0.5 | >5.0 | 4.24 |

TABLE VI-continued

| | | Antimicrobial Testing | | |
|---|---|---|---|---|
| | | Exposure Time | Log Reduction | |
| Sample | pH | (Minutes) | S. aureus | E. coli |
| (Glutaraldehyde/ | | 1.0 | >5.0 | >5.0 |
| Pentaerythritol) | | 2.0 | >5.0 | >5.0 |
| | | 5.0 | >5.0 | >5.0 |
| Ucarcide 250[1] | 8 | 0.5 | >5.0 | 3.92 |
| | | 1.0 | >5.0 | >5.0 |
| | | 2.0 | >5.0 | >5.0 |
| | | 5.0 | >5.0 | >5.0 |

[1]1-50% aqueous glutaraldehyde

Example 2 (glutaraldehyde/sucrose) was compared to Ucarcide 250 (50% aqueous glutaraldehyde) at their natural (pH's (pH 4) and at a buffered pH 8. The results of this test are listed in Table VI below. As Table VII indicates, Example 2 was very similar to the Ucarcide 250 at both natural pH's (pH 4) and at a buffered pH (pH 8) in its antimicrobial activity.

TABLE VII

| | | Antimicrobial Testing | | |
|---|---|---|---|---|
| | | Exposure Time | Log Reduction | |
| Sample | pH | (Minutes) | S. aureus | E. coli |
| Ex. 2 | 4 | 0.5 | 2.24 | 0.30 |
| (Glutaraldehyde/ | | 1.0 | 3.43 | 0.59 |
| Sucrose) | | 2.0 | >5.0 | 0.85 |
| | | 5.0 | >5.0 | 2.03 |
| Ucarcide 250 | 4 | 0.5 | 2.64 | 0.34 |
| | | 1.0 | 4.00 | 0.47 |
| | | 2.0 | >5.0 | 0.85 |
| | | 5.0 | >5.0 | 1.74 |
| Ex. 2 | 8 | 0.5 | >5.0 | 2.62 |
| | | 1.0 | >5.0 | 3.81 |
| | | 2.0 | >5.0 | >5.0 |
| | | 5.0 | >5.0 | >5.0 |
| Ucarcide 250 | 8 | 0.5 | >5.0 | 3.92 |
| | | 1.0 | >5.0 | >5.0 |
| | | 2.0 | >5.0 | >5.0 |
| | | 5.0 | >5.0 | >5.0 |

EXAMPLES 11-19

The composition of Example 2 (32.9 g of glutaraldehyde-sucrose) was blended with the absorbing agents of polyacrylate (20.0 g of Sanwet 3500p) and diatomaceous earth (147.1 g of Celatom FW-80) to formulate the composition of Example 11. The final composition ingredient amount (in wt-%) is listed in Table VIII below. Examples 12-19 were prepared by blending the ingredients listed in Table VIII to form absorbent blends containing Ucarcide 250 and Ucarcide 530g (glutaraldehyde absorbed on silicate) for comparative testing with the composition of Example 11.

A sanitizing test was performed on dry samples of Examples 11-19 against S. aureus with a 5 minute contact time. The formulations were tested 1:1 absorbent to inoculum. The results are listed in Table IX. As Table IX indicates Example 11 had good activity at 6 weeks at all three temperatures. Example 14 (Ucarcide 530G) at 3 week and 1 week samples had little activity with log reductions of S. aureus less than 1.0. The remaining Examples show no significant difference in Ucarcide 250 and 530g, but triethylene glycol (TEG), or TEG and nonylphenol ethoxylate were required for activity to be sustained.

TABLE VIII

| | Wt-% of Ingredient | | | | | | | | |
|---|---|---|---|---|---|---|---|---|---|
| Ingredient | Ex. 11 | Ex. 12 | Ex. 13 | Ex. 14 | Ex. 15 | Ex. 16 | Ex. 17 | Ex. 18 | Ex. 19 |
| Ex. 2 (Glut./Sucrose) | 16.46 | — | — | — | — | — | — | — | — |
| Ucarcide 250 | — | 8.0 | 8.0 | — | — | — | — | — | 8.0 |
| Ucarcide 530G[1] | — | — | — | 13.3 | 13.3 | 13.3 | 13.3 | 13.3 | — |
| Polyacrylate (Sanwet) | 10.0 | 10.0 | 10.0 | 10.0 | 10.0 | 10.0 | 10.0 | 10.0 | 10.0 |
| Diatomaceous Earth (FW-80) | 73.54 | 65.0 | 68.0 | 76.7 | 75.7 | 67.7 | 66.7 | 63.7 | 64.0 |
| Nonylphenol-ethoxylate | — | — | 1.0 | — | 1.0 | — | 1.0 | — | 1.0 |
| Triethylene Glycol | — | 9.0 | 9.0 | — | — | 9.0 | 9.0 | 9.0 | 9.0 |
| Silicate (Sipernat) | — | 8.0 | 4.0 | — | — | — | — | 4.0 | 8.0 |

[1]Glutaraldehyde absorbed on silicon dioxide.

TABLE IX

| Antimicrobial Testing of Examples 11-19 | | | |
|---|---|---|---|
| Example | Exposure Time (Minutes) | Weeks/Temp | Log Reduction S. aureus |
| 11 | 5 | Baseline | 2.84 |
| 11 | 5 | 6/40° C. | 2.68 |
| 11 | 5 | 6/50° C. | 3.20 |
| 12 | 5 | Baseline | 2.65 |
| 13 | 5 | Baseline | 3.60 |
| 14 | 5 | Baseline | 0.28 |
| 14 | 5 | 3/RT[1] | 0.25 |
| 14 | 5 | 1/RT | 0.39 |
| 14 | 5 | 1/40° C. | 0.09 |
| 14 | 5 | 1/50° C. | 0.10 |
| 15 | 5 | Baseline | 0.15 |
| 16 | 5 | Baseline | 2.10 |
| 17 | 5 | Baseline | 2.53 |
| 18 | 5 | Baseline | 1.94 |
| 19 | 5 | Baseline | 2.50 |

[1]RT = Room Temperature

A sanitizing test was conducted on Examples 11, 12-13, and 16-18 against S. aureus with a 5 minute contact time. The formulations tested were 1:1 absorbent to inoculum. The results are listed in Table X below. As Table X indicates, the ten week stability formulation of Example 11 continued to give good activity regardless of temperature. The four week stability samples of the other Examples showed good activity with a 2.5 log reduction in S. aureus or greater.

TABLE X

| Antimicrobial Testing | | | |
|---|---|---|---|
| Example | Exposure Time (Minutes) | Weeks/Temp | Log Reduction S. aureus |
| 11 | 5 | 10/RT[1] | 3.62 |
| 11 | 5 | 10/40° C. | 2.71 |

TABLE X-continued

| | Antimicrobial Testing | | |
|---|---|---|---|
| Example | Exposure Time (Minutes) | Weeks/Temp | Log Reduction S. aureus |
| 11 | 5 | 10/50° C. | 3.59 |
| 12 | 5 | 4/RT | 3.22 |
| 13 | 5 | 4/RT | 3.87 |
| 16 | 5 | 4/RT | 2.89 |
| 17 | 5 | 4/RT | 2.84 |
| 18 | 5 | 4/RT | 2.48 |

[1]RT = Room Temperature

EXAMPLE 20

Example 20 was made in the same way as Example 1 except that an absorbing agent was blended with the composition of Example 1 to produce a moisture absorbent antimicrobial composition. The composition of Example 1 was blended with Hubersorb, a moderately basic sodium silicate to formulate the composition of Example 20 in the amounts indicated in Table XI. The composition of Example 20 was then tested for its antimicrobial activity using the identical procedure as that in Example 1 except that the composition of Example 20 was employed in polyvinyl alcohol packets. Example 20 was tested by comparison with Ucarcide 250 absorbed on sodium silicate (Ucarcide blend) in the amounts indicated in Table XII. The test samples were aged for 2 weeks at 50° C. and at 50% relative humidity in a loosely closed container. As Table XII indicates, the absorbed Ucarcide blend lost most of its activity while the moisture absorbent blend of Example 20 had outstanding antimicrobial activity against both gram negative (E. coli) and gram positive (S. aureus) bacteria.

TABLE XI

| Sample | Sodium Silicate | Ucarcide 250 | Glutaraldehyde/ Sucrose |
|---|---|---|---|
| Example 20 | 84.6% | — | 15.4% |
| Ucarcide blend | 75.0% | 25.0% | — |

TABLE XII

| | Antimicrobial Testing of Example 20 | | |
|---|---|---|---|
| | Exposure Time | Log Reductions | |
| Sample | (Minutes) | S. Aureus | E. Coli |
| Example 20[1] | 0.5 | >5.00 | 4.48 |
| | 1.0 | >5.00 | >5.00 |
| | 2.0 | >5.00 | >5.00 |
| | 5.0 | >5.00 | >5.00 |
| Ucarcide Blend[2] | 0.5 | 0.02 | 0.24 |
| | 1.0 | 0.22 | 0.15 |
| | 2.0 | 0.22 | 0.18 |
| | 5.0 | 0.20 | 0.30 |

[1]Example 1 blended with sodium silicate and used at theoretical 1250 ppm
[2]Aqueous glutaraldehyde absorbed on sodium silicate and used at 1250 ppm

EXAMPLE 21

A glutaraldehyde/sucrose adduct was prepared in a similar manner to Example 1. The composition contained 26% glutaraldehyde by weight from titration. (Similar to Example 1). This composition was used in an amount of 0.602 grams in packets made of polyvinyl alcohol (PVA) material. The composition was employed alone in a packet, was blended with Sipernat 50 (a silicate, pH 7), and blended with Hubersorb 600 (a sodium silicate, pH 9-10). The packets were dissolved in 125 mm. of water to produce 1250 ppm (theoretical) aqueous glutaraldehyde solutions. Solutions were tested against S. aureus and E. coli with exposure times of 30 seconds, 60 seconds, 120 seconds, and 300 seconds. The packets were aged at 50° C. in loosely capped bottles in ovens at 50% relative humidity.

One sample contained 0.602 grams of the glutaraldehyde/sucrose composition (Ex. 1) alone employed in a PVA packet. Another sample contained 0.602 grams of the glutaraldehyde/sucrose composition combined with 3.3 grams of Sipernat 50. A further sample contained 0.602 grams of the glutaraldehyde/sucrose composition combined with 3.3 grams of Hubersorb 600. The above samples were compared with Ucarcide 250/absorbing agent compositions. The results of the antimicrobial study are listed in Table XIII below.

As Table XIII indicates, the absorbed Ucarcide blends lost much of their activity over time. However, the glutaraldehyde/sucrose absorbent blends had outstanding antimicrobial activity against both E. coli and S. aureus bacteria at 6 weeks when Hubersorb was employed as the absorbing agent. When the glutaraldehyde/sucrose composition was employed alone in a PVA packet, outstanding antimicrobial activity was achieved within 2 to 5 minutes.

TABLE XIII

| | Antimicrobial Testing with PVA Packets | | | |
|---|---|---|---|---|
| | Exposure Time | Weeks | Log Reduction | |
| Sample | (Minutes) | at 50° C. | S. aureus | E. coli |
| Ucarcide 250 | 0.50 | 0 | 3.82 | 0.54 |
| on Sipernat 50 | 1.0 | 0 | >5.0 | 0.88 |
| | 2.0 | 0 | >5.0 | 2.01 |
| | 5.0 | 0 | >5.0 | >5.0 |
| Ucarcide 250 | 0.5 | 0 | 3.28 | 0.93 |
| on Hubersorb | 1.0 | 0 | 3.20 | 1.17 |
| | 2.0 | 0 | 4.72 | 2.96 |
| | 5.0 | 0 | >5.0 | >5.0 |
| Glut./Sucrose | 0.5 | 0 | 2.12 | 0.74 |
| Sipernat 50 | 1.0 | 0 | 3.42 | 0.81 |
| | 2.0 | 0 | 4.49 | 1.87 |
| | 5.0 | 0 | >5.0 | 4.23 |
| Glut./Sucrose | 0.5 | 0 | 3.58 | 3.70 |
| Hubersorb | 1.0 | 0 | >5.0 | >5.0 |
| | 2.0 | 0 | >5.0 | >5.0 |
| | 5.0 | 0 | >5.0 | >5.0 |
| Ucarcide 250 | 0.5 | 6 | 0.25 | 0.05 |
| on Sipernat 50 | 1.0 | 6 | 0.38 | 0.07 |
| | 2.0 | 6 | 0.45 | 0.17 |
| | 5.0 | 6 | 0.38 | 0.12 |
| Ucarcide 250 | 0.5 | 6 | 0.27 | 0.05 |
| on Hubersorb | 1.0 | 6 | 0.24 | 0.12 |
| | 2.0 | 6 | 0.33 | 0.17 |
| | 5.0 | 6 | 0.38 | 0.22 |
| Glut./Sucrose | 0.5 | 6 | 0.10 | 0.26 |
| Sipernat 50 | 1.0 | 6 | 0.16 | 0.33 |
| | 2.0 | 6 | 0.11 | 0.48 |
| | 5.0 | 6 | 0.21 | 0.87 |
| Glut./Sucrose | 0.5 | 6 | >5.0 | >5.0 |
| Hubersorb | 1.0 | 6 | >5.0 | >5.0 |
| | 2.0 | 6 | >5.0 | >5.0 |
| | 5.0 | 6 | >5.0 | >5.0 |
| Glut./Sucrose | 0.5 | 6 | 1.80 | 0.51 |
| (Alone | 1.0 | 6 | 2.57 | 1.52 |
| in PVA) | 2.0 | 6 | >5.0 | 3.91 |
| | 5.0 | 6 | >5.0 | >5.0 |

EXAMPLES 22-34

The hemiacetals of Examples 22 through 34 were made by a similar procedure as described in Example 1. Table XIV is a summary of the products of Examples 22-34, and shows the hemiacetals of the dialdehyde, as well as a brief description of the resulting products including the physical states of matter and the stability of these products after six weeks storage at 40° C. Two important criteria from a practical standpoint are the stability, i.e., the percent loss of glutaraldehyde and the glutaraldehyde content of the product. The loss factors determines the shelf-life to ensure reliability in performance on aging and the high glutaraldehyde content provides the potential to formulate an economical product in concentrated forms. Generally, the most ideal form of the dialdehyde donor is a solid form as this would reduce the tendency of the interaction with other components in the final product. Referring to Table XIV again, although the Neodol 25-12(TM) hemiacetal provides a reasonably stable hemiacetal, the sucrose hemiacetal is preferred because it is not only more stable, but has a substantially higher dialdehyde content. The pentaerythritol hemiacetal is also preferred since it has a very high dialdehyde content as well as good stability.

The sucrose derivative in the closed bottle (FIG. 2) showed a very slight, almost imperceptible loss of glutaraldehyde after eight weeks whereas by comparison the glycerol derivative lost approximately 40 percent of its glutaraldehyde content. In the open bottle (FIG. 3) the sucrose derivative did not lose any glutaraldehyde whereas the glycerol derivative lost approximately 50 percent after eight weeks. Thus, the sucrose derivative showed a surprising and unexpected stability at the 40° C. storage condition. The 40° C. storage is a realistic temperature for example during shipping and storage unless the product is stored in an air conditioned atmosphere.

Figure 4:
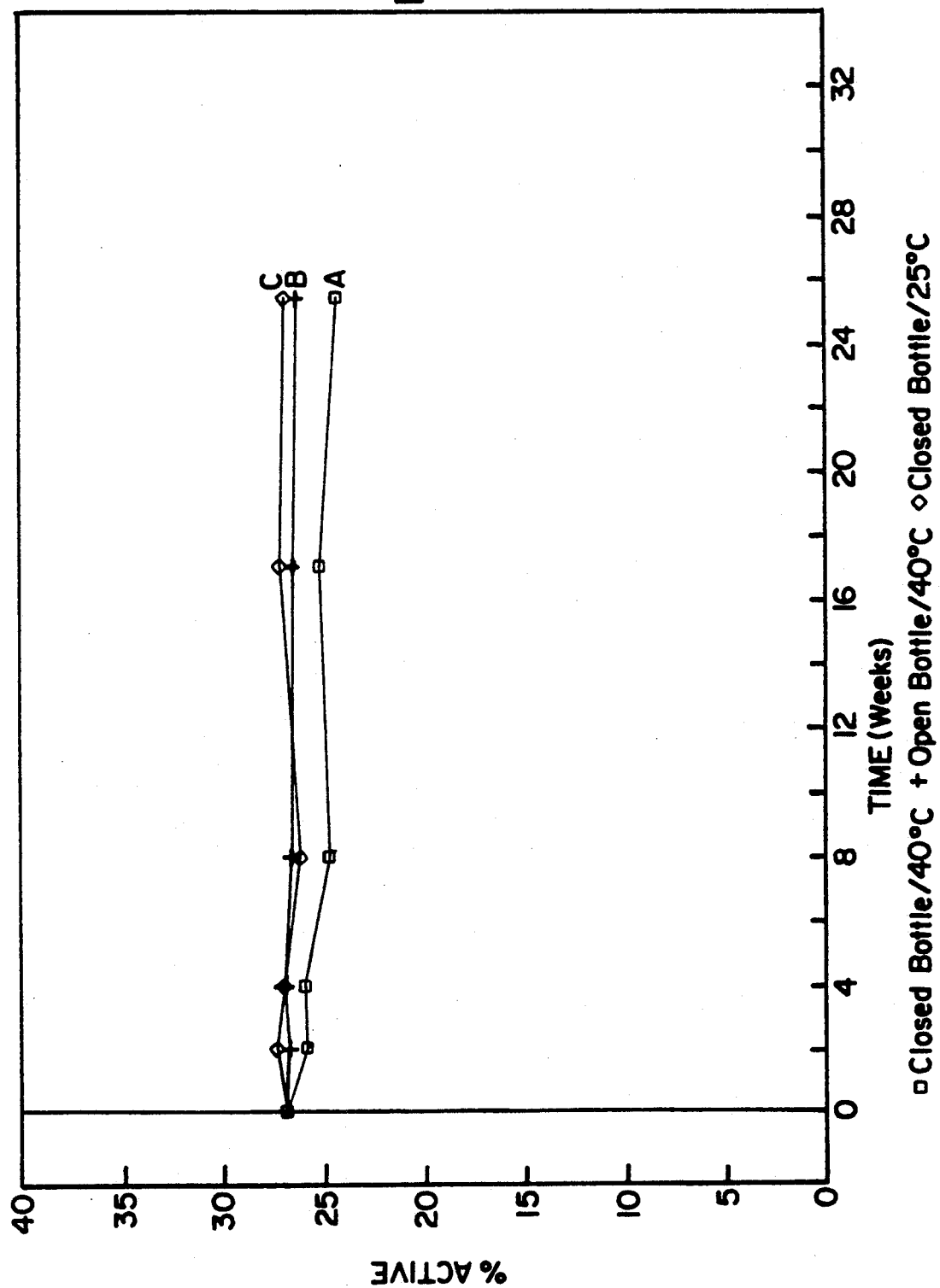
FIG. 4 is a graph demonstrating the relative stabilities of a sucrose-glutaraldehyde hemiacetal of the invention in various storage conditions.

Next, an extended storage test was conducted wherein samples of the sucrose-glutaraldehyde hemiacetal were stored for 6 months at 40° C. and at room temperature. The 40° C. samples were stored in open and closed bottles as before. FIG. 4 is a summary of this data with the ordinate expanded to show up any small differences between the samples. This data indicates

TABLE XIV

| Ex. | Glutaraldehyde Adduct | Physical State | Initial Corrected Activity | Activity After 6 Wks/40° C. | Loss in Activity | Percentage Loss |
| --- | --- | --- | --- | --- | --- | --- |
| 22 | Sucrose | S[1] | 26.4 | 24.63 | 1.77 | 6.7 |
| 23 | Neodol25-12 | S | 4.55 | 4.14 | 0.41 | 9.0 |
| 24 | 1,4-Cyclohexane diol | L[2] | 36.1 | 31.9 | 4.2 | 11.6 |
| 25 | Pentaerythritol | S | 51.8 | 44.7 | 7.0 | 13.7 |
| 26 | Sugar Ester | S | 3.64 | 3.14 | 0.5 | 13.7 |
| 27 | Glucose | S/L | 18.4 | 14.98 | 3.42 | 18.6 |
| 28 | Fructose | S/L | 29.2 | 23.65 | 5.55 | 19.0 |
| 29 | Lactose | S | 18.7 | 14.89 | 3.81 | 20.0 |
| 30 | Ethylene glycol | L | 43.1 | 21.6 | 21.5 | 21.6 |
| 31 | Glycerol | L | 44.8 | 32.68 | 12.1 | 27.0 |
| 32 | Inositol | S | 22.6 | 13.4 | 9.2 | 40.7 |
| 33 | Sorbitol | S | 27.7 | 10.8 | 16.9 | 61.0 |
| 34 | Mannitol | S | 28.5 | 3.62 | 24.88 | 87.3 |

[1]Solid
[2]Liquid

While we do not wish to be bound by any theory, we have found that solid hemiacetals in general appear to be more stable than liquid hemiacetals. Stereochemical configuration appears to also be a factor in stability in that differences exist among the different hemiacetals within both groups. The most preferred hemiacetal of those shown is the sucrose hemiacetal since it is a solid, having a high dialdehyde content, and since sucrose is an inexpensive commodity chemical available in a very pure form so that further purification is not required.

EXAMPLE 35

Figure 2:
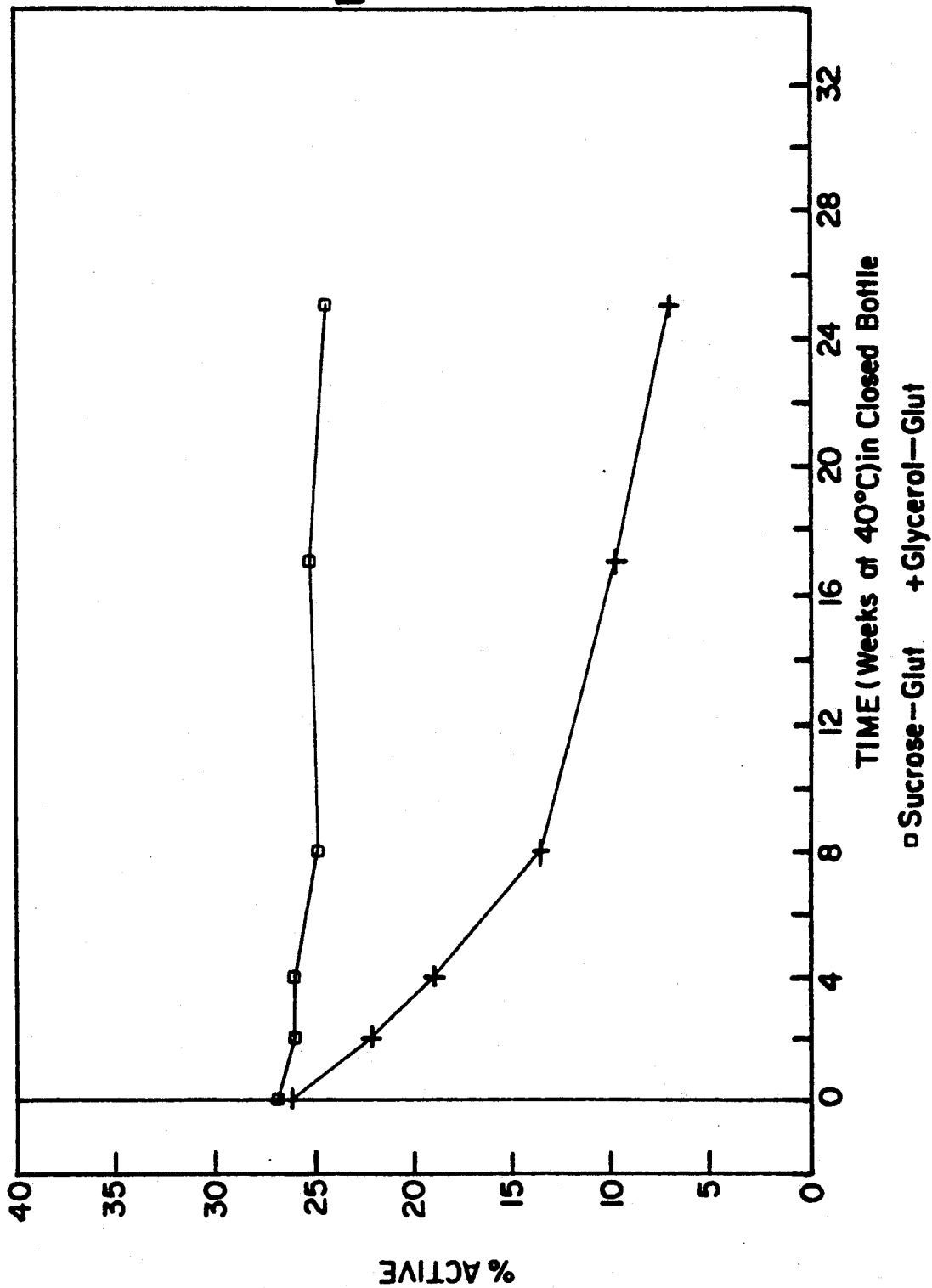
FIG. 2 is a graph demonstrating the relative stabilities of the sucrose-glutaraldehyde hemiacetal compared to a prior art glycerol-glutaraldehyde hemiacetal in a closed bottle at 40° C.
Figure 3:
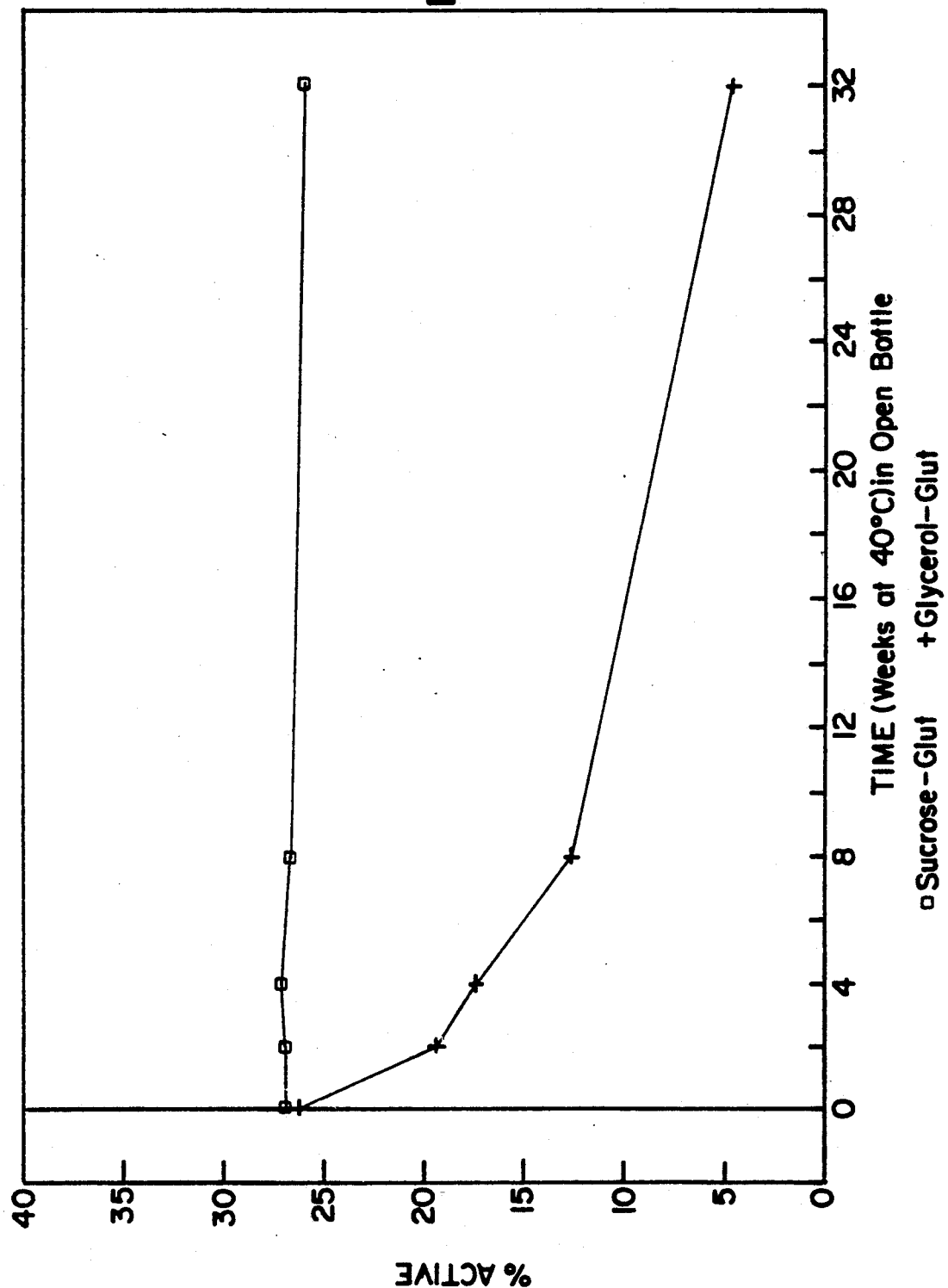
FIG. 3 is a graph demonstrating the relative stabilities of the sucrose-glutaraldehyde hemiacetal compared to a prior art glycerol-glutaraldehyde hemiacetal in an open bottle at 40° C.

FIGS. 1, 2 and 3 in the drawings show the relative stabilities of a sucrose-glutaraldehyde hemiacetal of the invention compared to a prior art glycerol-glutaraldehyde hemiacetal under various storage conditions. FIG. 1 shows that at room temperature the sucrose-glutaraldehyde hemiacetal showed no detectable loss of glutaraldehyde in eight weeks whereas the glycerol-glutaraldehyde hemiacetal lost about 10 percent glutaraldehyde. FIGS. 2 and 3 show the relative stabilities of the sucrose-glutaraldehyde hemiacetal and glycerol-glutaraldehyde hemiacetal at 40° C. FIG. 2 shows the data for storage in a closed bottle and FIG. 3 shows the data for storage in an open bottle. These two conditions, ie., the open bottle and closed bottle, would show any effect of humidity on the stabilities of the hemiacetals.

that at room temperature (closed bottle) virtually no glutaraldehyde was lost. Likewise at 40° C. and open bottle, virtually no glutaraldehyde was lost. At the 40° C. closed bottle condition, approximately 5 to 6 percent glutaraldehyde was lost. The stability data confirms that the sucrose-glutaraldehyde hemiacetal is indeed very stable.

EXAMPLE 36

In order to demonstrate the bactericidal effectiveness of the various polyol-glutaraldehyde hemiacetals, various hemiacetals were synthesized and compared with glutaraldehyde itself at the same active glutaraldehyde levels. The bactericidal test method used was the standard A.O.A.C. test method. The test organisms used were *S. aureus* and *E. coli*. The tests were conducted at the natural pH of the compound as well as at pH 8.0 where glutaraldehyde products are usually tested because of its optimal condition with respect to its bactericidal activity. Table XV is a summary of the glutaraldehyde hemiacetal derivatives of pentaerythritol, sucrose and lactose at the natural pH's of the derivatives compared to 50% aqueous glutaraldehyde (Ucarcide 250). Within experimental error, these derivatives behave identical to glutaraldehyde in it bactericidal behavior. Table XVI is a repeat of Table XV, except that the pH's were all adjusted to pH 8. Without exception, these hemiacetals within experimental error again show bactericidal properties identical to the free glutaraldehyde.

analysis similar to Union Carbide's analytical procedure for glutaraldehyde using sodium bisulfite (BB-TL-2004) was used to measure the activity of the sucrose-

TABLE XV

| | BACTERICIDAL TEST (NATURAL pH's) | | | | | | | |
|---|---|---|---|---|---|---|---|---|
| EXPOSURE | PENTAERYTHRITOL DERIVATIVES | | SUCROSE DERIVATIVE | | LACTOSE DERIVATIVE | | (50% Aq GWT) Ucarcide 250 | |
| TIMES (Minutes) | S. aureus | E. coli | S. aureus | E. coli | S. aureus | E. coli | S. aureus | E. coli |
| 0.5 | 1.62 | 0.27 | 2.24 | 0.30 | — | — | 2.64 | 0.34 |
| 1.0 | 2.33 | 0.39 | 3.43 | 0.59 | — | — | 4.00 | 0.47 |
| 2.0 | 4.09 | 0.59 | >5.0 | 0.85 | — | — | >5.0 | 0.85 |
| 5.0 | >5.0 | 1.30 | >5.0 | 2.03 | — | — | >5.0 | 1.74 |
| | pH 4 | | pH 4 | | | | pH 4 | |

Concentration: 1250 ppm on the basis of glutaraldehyde

TABLE XVI

| | BACTERICIDAL TEST (pH 8) | | | | | | | |
|---|---|---|---|---|---|---|---|---|
| EXPOSURE | PENTAERYTHRITOL DERIVATIVES | | SUCROSE DERIVATIVE | | LACTOSE DERIVATIVE | | (50% Aq GWT) Ucarcide 250 | |
| TIMES (Minutes) | S. aureus | E. coli | S. aureus | E. coli | S. aureus | E. coli | S. aureus | E. coli |
| 0.5 | >5.0 | 4.24 | >5.0 | 2.62 | >5.0 | 4.28 | >5.0 | 3.92 |
| 1.0 | >5.0 | >5.0 | >5.0 | 3.81 | >5.0 | >5.0 | >5.0 | >5.0 |
| 2.0 | >5.0 | >5.0 | >5.0 | >5.0 | >5.0 | >5.0 | >5.0 | >5.0 |
| 5.0 | >5.0 | >5.0 | >5.0 | >5.0 | >5.0 | >5.0 | >5.0 | >5.0 |
| | pH 8 | | pH 8 | | pH 8 | | pH 8 | |

Concentration: 1250 ppm on the basis of glutaraldehyde

EXAMPLE 37

Commercial aqueous samples of glutaraldehyde were analyzed using 13-C NMR by Whipple. At room temperature 70% of the active material existed in the 2,6-dihydroxypyran structures with the remainder as free glutaraldehyde and its hydrates. Glutaraldehyde has a strong tendency to hydrate and subsequently cyclize to these ring structures.

We found that concentrated aqueous or anhydrous solutions of glutaraldehyde mixed with low molecular weight alcohols, polyols or carbohydrates contained an equilibrium mixture. The mixture contained glutaraldehyde, its water hydrates, and adducts with analogous structures as aqueous glutaraldehyde. The alcohols, polyols or carbohydrates replaced the water of the 2,6-dihydroxypyrans and the glutaraldehyde hydrates in the adducts to form hemiacetal derivatives. As water was removed or the mole ratio of alcohol, polyol or carbohydrate to glutaraldehyde was increased, the mixture became enriched with adducts.

The structure of these adducts was determined by 13-C NMR. Several 13-C NMR were taken on a sucrose-glutaraldehyde adduct. In a solid state 13-C NMR of anhydrous sucrose-glutaraldehyde hemiacetal adduct there was an almost complete absence of a carbonyl absorbance near 200 ppm. The other absorptions were broad due to the nature of this method. This indicated that all the glutaraldehyde was complexed with the sucrose. A 13-C NMR spectra in dimethylsulfoxide-d6 of the anhydrous sucrose-glutaraldehyde adduct showed a marked increase in the carbonyl absorption (near 200 pp ) and indicated the presence of free glutaraldehyde. The hemiacetal bonds were apparently weak enough to release some free glutaraldehyde in dimethylsulfoxide solution. The spectra in dimethylsulfoxide-d6 also showed the broad absorptions assigned to the hemiacetal carbons.

Wet chemical analysis of these adducts was used to supplement the NMR spectral method. A chemical glutaraldehyde adduct. A small amount of the solid adduct was dissolved in water producing a 500 ppm solution. The solution was analyzed for its glutaraldehyde content and this value was used to calculate the activity of the solid. This method can be used to measure the hemiacetal adduct. Since the hemiacetal form will hydrolyze to form free glutaraldehyde in water and acetal adducts will not hydrolyze under these conditions, the analytical method will only measure the hemiacetal forms.

EXAMPLES 38–42

In order to demonstrate the sterilant activity of the composition of the invention, Examples 38–42 were prepared by a similar procedure as described in Example 1. Table XVII is a summary of the ingredients of Examples 38–42. Each of the examples contained the glutaraldehyde-sucrose hemiacetal of the invention, with a buffering agent (sodium bicarbonate) employed in Examples 39–42 and a nonionic surfactant employed in Examples 40 and 42. Each sample made was placed in water soluble polyvinyl alcohol packaging and the Examples were tested for their sterilant activity.

TABLE XVII

| | Wt.-% of Ingredient | | | | |
|---|---|---|---|---|---|
| Ingredient | Ex. 38 | Ex. 39 | Ex. 40 | Ex. 41 | Ex. 42 |
| Glutar./Sucrose | 100.00 | 98.46 | — | 97.56 | — |
| Sodium Bicarbonate | — | 1.54 | 1.55 | 2.44 | 26.84 |
| Glutar./Sucrose[1] | — | — | 98.45 | — | 73.16 |
| TOTAL | 100.00 | 100.00 | 100.00 | 100.00 | 100.00 |

[1]with 0.5% Neodol 25-12 (nonionic surfactant)

The test method employed for determining the sterilant activity of Examples 38–42 was that disclosed in "Sporicidal Activity of Disinfectants", A.O.A.C. Methods of Analysis, 15th Edition, 1990. The test was conducted at a temperature of 20° C. The test organism used was *Bacillus subtilis*. All of the Examples analyzed, including a control sample of commercial liquid glutaraldehyde, provided 20,000 ppm active glutaraldehyde upon dilution in deionized water. The results of the sterilant test are summarized in Table XVIII below.

TABLE XVIII

Sterilant Activity of Examples 38-42

| Example | Exposure Time (Hours) | pH | # Negative Tubes/ # Tubes Tested |
|---------|----------------------|------|--------------------------------|
| 38 | 6 | 4.02 | 30/30 |
| 39 | 6 | 7.48 | 30/30 |
| 40 | 6 | 7.72 | 30/30 |
| 41 | 6 | 8.27 | 30/30 |
| 42 | 6 | 8.20 | 30/30 |
| 42 | 2 | 8.27 | 30/30 |
| Control[1] | 6 | 7.70 | 30/30 |

[1]Control is commerical liquid glutaraldehyde product.

As Table XVIII indicates, the glutaraldehyde-sucrose composition provides sterilant activity equivalent to or better than commercial glutaraldehyde and can be supplied in water soluble packaging. Of 30 tubes tested, all 30 tubes were negative in that there was no growth in the tubes. Therefore, there was a total kill or sterilization of the tested microorganism. Also, as can be seen in Table XVIII, use of the composition as a sterilant is not as dependent on pH since the exposure time is in hours to obtain total kill of all microorganisms.

The foregoing discussion and Examples are illustrative of the invention. However, since many embodiments of the invention can be made without departing from the spirit and scope of the invention, the invention resides wholly in the claims hereinafter appended.

We claim:

1. A solid, antimicrobial composition comprising:
   (a) an effective amount of an antimicrobial dialdehyde compound;
   (b) an effective stabilizing amount of a polyhydroxy compound comprising a carbohydrate compound, a polyol compound comprising a sugar alcohol, or mixtures thereof, said carbohydrates selected from the group consisting of a monosaccharide compound, a disaccharide compound, an oligosaccharide compound, derivatives thereof, and mixtures thereof; and
   (c) an effective amount of a buffering agent for maintaining a pH for optimum antimicrobial activity when said composition is employed in an active antimicrobial form;
   wherein said antimicrobial dialdehyde is released in an active antimicrobial form when said composition is contacted with an aqueous liquid.

2. The composition of claim 1 wherein a —CHO group in said anitmicrobial dialdehyde reacts with a —OH group in said polyhydroxy compound to bond said agent to said polyhydroxy compound.

3. The composition of claim 1 wherein said carboxhydrate compound comprises an ester derivative or an ether derivative of said carbohydrate.

4. The composition of claim 1 wherein said antimicrobial dialdehyde comprises glutaraldehyde.

5. The composition of claim 4 wherein said composition comprises about 1 to 90 wt-% of said glutaraldehyde.

6. The composition of claim 1 wherein said carbohydrate compound comprises a disaccharide, an oligosaccharide, or mixtures thereof, that comprise repeating units of glucose.

7. The composition of claim 1 wherein said monosaccharide compound comprises fructose, glucose, derivatives thereof, or mixtures thereof.

8. The composition of claim 1 wherein said disaccharide compound comprises sucrose, lactose, maltose, derivatives thereof, or mixtures thereof.

9. The composition of claim 1 wherein said polyol comprises pentaerythritol, mannitol, sorbitol, inositol, or mixtures thereof.

10. The composition of claim 1 wherein said composition comprises about 10 to 99 wt-% of said polyhydroxy compound.

11. The composition of claim 1 wherein said composition has a pH of about 3 to 11 when in activated form.

12. The composition of claim 1 wherein said buffering agent is selected from the group consisting of sodium bicarbonate/sodium carbonate, acetic acid/ sodium acetate, and potassium dihydrogen phosphate/disodium hydrogen phosphate.

13. The composition of claim 1 wherein said composition is in solid particulate form.

14. The composition of claim 1 wherein said composition is a solid block.

15. A solid, antimicrobial composition for preserving sanitizing, disinfecting or sterilizing a contaminated surface or area, said composition comprising:
   (a) about 1 to 90 wt-% of an antimicrobial agent having the following formula: OHC—R—CHO, wherein R comprises a $C_1$ to $C_4$ alkylene group or a single covalent bond;
   (b) about 10 to 99 wt-% of a polyhydroxy compound comprising a carbohydrate compound, a polyol compound comprising a sugar alcohol, or mixtures thereof, said carbohydrate selected from the group consisting of a monosaccharide compound, a disaccharide compound, an oligosaccharide compound, derivatives thereof, and mixtures thereof; and
   (c) about 1 to 30 wt-% of a buffering agent that can maintain a pH of about 3 to 11 for optimum antimicrobial activity of said composition when said composition is in activated form;
   wherein said antimicrobial dialdehyde is released in an active antimicrobial form when said composition is contacted with an aqueous liquid.

16. The composition of claim 15 wherein said dialdehyde compound comprises glutaraldehyde.

17. The composition of claim 15 wherein said monosaccharide compound comprises fructose, glucose, derivatives thereof, or mixtures thereof.

18. The composition of claim 15 wherein said disaccharide compound comprises sucrose, lactose, maltose, or mixtures thereof.

19. The composition of claim 15 wherein said polyol comprises pentaerythritol, mannitol, sorbitol, inositol, or mixtures thereof.

20. The composition of claim 15 wherein said buffering agent is selected from the group consisting of sodium bicarbonate/sodium carbonate, acetic acid/sodium acetate, and potassium dihydrogen phosphate/disodium hydrogen phosphate.

21. The composition of claim 15 further comprising about 0 to 89 wt-% of a surfactant.

22. The composition of claim 15 wherein said composition is in solid particulate form.

23. The composition of claim 15 wherein said composition is a solid block.

24. A solid, stable antimicrobial hemiacetal composition comprising:

(a) about 1 to 90 wt-% of glutaraldehyde; and
(b) about 10 to 99 wt-% of sucrose;
wherein said glutaraldehyde is released in an active antimicrobial form when said composition is contacted with an aqueous liquid.

25. A method of preserving, sanitizing, disinfecting or sterilizing a contaminated surface or area using a stable antimicrobial composition comprising the step of contacting said composition in activated form with said contaminated surface or area for a period of time effective to preserve, sanitize, disinfect or sterilize said surface or area; said composition comprising:
(a) an effective amount of an antimicrobial dialdehyde compound; and
(b) an effective stabilizing amount of a polyhydroxy compound comprising a carbohydrate compound, a polyol compound comprising a sugar alcohol, or mixtures thereof, said carbohydrate selected from the group consisting of a monosaccharide compound, a disaccharide compound, an oligosaccharide compound, derivatives thereof, and mixtures thereof;
wherein said antimicrobial dialdehyde is released in an active antimicrobial form when said composition is contacted with an aqueous liquid.

26. The method of claim 25 wherein a —CHO group in said antimicrobial dialdehyde reacts with a —OH group in said polyhydroxy compound to bond said agent to said polyhydroxy compound.

27. The method of claim 25 wherein said carbohydrate compound comprises an ester derivative or an ether derivative of said carbohydrate.

28. The method of claim 25 wherein said antimicrobial dialdehyde comprises glutaraldehyde.

29. The method of claim 28 wherein said composition comprises about 1 to 90 wt-% of said glutaraldehyde.

30. The method of claim 25 wherein said carbohydrate compound comprises a disaccharide, an oligosaccharide, or mixtures thereof, that comprise repeating units of glucose.

31. The method of claim 25 wherein said monosaccharide compound comprises fructose, glucose, derivatives thereof, or mixtures thereof.

32. The method of claim 25 wherein said disaccharide compound comprises sucrose, lactose, maltose, derivatives thereof, or mixtures thereof.

33. The method of claim 25 wherein said polyol comprises pentaerythritol, mannitol, sorbitol, inositol, or mixtures thereof.

34. The method of claim 25 wherein said composition comprises about 10 to 99 wt-% of said polyhydroxy compound.

35. The method of claim 25 wherein said antimicrobial composition further comprises a buffering agent.

36. The method of claim 25 wherein said composition has a pH of about 3 to 11 when in activated form.

37. The method of claim 25 wherein said composition is in solid particulate form.

38. The method of claim 25 wherein said composition is a solid block.

39. A method of preserving, sanitizing, disinfecting or sterilizing a contaminated surface or area using a stable antimicrobial composition comprising the step of contacting said composition in activated form with said contaminated surface or area for a period of time effective to preserve, sanitize, disinfect or sterilize said surface or area; said composition comprising:
(a) about 1 to 90 wt-% of an antimicrobial agent having the following formula: OHC—R—CHO, wherein R comprises a $C_1$ to $C_4$ alkylene group or a single covalent bond;
(b) about 10 to 99 wt-% of a polyhydroxy compound comprising a carbohydrate compound, a polyol compound comprising a sugar alcohol, or mixtures thereof, said carbohydrate selected from the group consisting of a disaccharide compound, an oligosaccharide compound, and mixtures thereof; and
(c) about 0 to 30 wt-% of a buffer that can maintain a pH for optimum antimicrobial activity of said composition when said composition is in activated form;
wherein said antimicrobial dialdehyde is released in an active antimicrobial form when said composition is contacted with an aqueous liquid.

40. The method of claim 39 wherein said dialdehyde compound comprises glutaraldehyde.

41. The method of claim 39 wherein said disaccharide compound comprises sucrose, lactose, maltose, or mixtures thereof.

42. The method of claim 39 wherein said polyol comprises pentaerythritol, mannitol, sorbitol, inositol, or mixtures thereof.

43. The method of claim 39 wherein said buffer is selected from the group consisting of sodium bicarbonate/sodium carbonate, acetic acid/sodium acetate, and potassium dihydrogen phosphate/disodium hydrogen phosphate.

44. The method of claim 39 wherein said composition is in solid particulate form.

45. The composition of claim 24 further comprising glycerol.

46. The method of claim 39 wherein said composition is a solid block.

* * * * *